United States Patent [19]

Meyer et al.

[11] 4,002,762

[45] Jan. 11, 1977

[54] 2-AMINO-3,4-DIHYDROPYRIDINES USED TO EFFECT CORONARY VESSEL DILATION AND TREAT HYPERTENSION

[75] Inventors: Horst Meyer; Friedrich Bossert; Wulf Vater, all of Wuppertal; Kurt Stoepel, Opladen, all of Germany

[73] Assignee: Bayer Aktiengesellschaft, Germany

[22] Filed: Jan. 28, 1975

[21] Appl. No.: 544,934

Related U.S. Application Data

[62] Division of Ser. No. 445,166, Feb. 25, 1974.

[30] Foreign Application Priority Data

Mar. 3, 1973 Germany .......................... 2310747

[52] U.S. Cl. ................. 424/266; 424/251; 424/258; 424/263
[51] Int. Cl.² ...................................... A61K 31/455
[58] Field of Search ............. 424/266; 260/295.5 R

[56] References Cited

UNITED STATES PATENTS

| | | | |
|---|---|---|---|
| 3,708,489 | 1/1973 | Rucker et al. | 260/295.5 R |
| 3,773,773 | 11/1973 | Bossert | 260/295.5 R |
| 3,775,422 | 11/1973 | Bossert et al. | 260/294.9 |
| 3,925,395 | 12/1975 | Meyer et al. | 260/294.8 G |

*Primary Examiner*—Leonard Schenkman

[57] ABSTRACT

3-Substituted 2-amino-3,4-dihydropyridine-3-carboxylic acid esters are produced by reacting 2-amino-1,4-dihydropyridine-3-carboxylic acid esters with an alkylating agent in the presence of an inert organic solvent at a temperature of from 20° C to 200° C. The compounds, of which 2-amino-3,6-dimethyl-4-phenyl-3,4-dihydropyridine-3,5-dicarboxylic acid diethyl ester is a typical embodiment, possess antihypertensive and coronary dilating properties.

34 Claims, No Drawings

2-AMINO-3,4-DIHYDROPYRIDINES USED TO EFFECT CORONARY VESSEL DILATION AND TREAT HYPERTENSION

This is a division of copending application Ser. No. 445,166, filed Feb. 25, 1974.

The present invention relates to 2-amino-3,4-dihydropyridines, to a novel process for their production, to pharmaceutical compositions useful for their antihypertensive effect and coronary dilating effect using said compounds as the active agent, and to methods of treating hypertension in humans and animals and methods of effecting coronary dilation in humans and animals using said compounds.

It is known in the art that the reaction of glutaronitriles with hydrogen halides and subsequent elimination of hydrogen halide produces 2-amino-3,4-dihydropyridines:

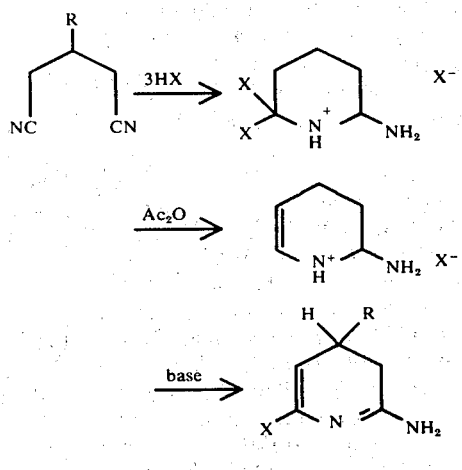

wherein
X is chloro, bromo or iodo; and
R is hydrogen, or phenyl (compare L. G. Duquette and F. Johnson, Tetrahedron 23, 4517 (1967)).

However, to date nothing has been disclosed concerning 3,4-dihydropyridines which are amino-substituted in the 2- or the 2- and 6-positions and have carbonylic groups in the 3- and 5-positions.

More specifically the present invention is concerned with 2-amino-3,4-dihydropyridines of the formula:

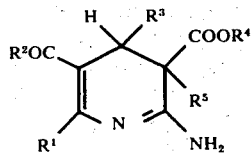

wherein $R^1$ is hydrogen, straight or branched chain lower alkyl, or amino;

$R^2$ is straight or branched chain lower alkyl or $OR'$ wherein $R'$ is a straight or branched chain saturated, partially unsaturated, or unsaturated lower hydrocarbon, or said hydrocarbon interrupted by 1 or 2 oxygen atoms;

$R^3$ is a straight chain, branched chain, or cyclic unsaturated, partially unsaturated, or unsaturated hydrocarbon of up to 6 carbon atoms; aryl of 6 to 10 carbon atoms unsubstituted or substituted by 1, 2 or 3 of the same or different substituents selected from the group consisting of alkyl of 1 to 4 carbon atoms, alkoxy of 1 to 4 carbon atoms, halogen, azido, cyano, phenyl, nitro, trifluoromethyl, carbalkoxy of 1 to 4 carbon atoms in the alkoxy moiety and $SO_n$-alkyl of 1 to 4 carbon atoms in the alkyl moiety wherein $n$ is 0, 1 or 2; quinolyl; isoquinolyl; pyridyl; pyrimidyl; thenyl; furyl; or pyrryl;

$R^4$ is a straight or branched chain saturated, partially unsaturated, or unsaturated hydrocarbon of 1 to 6 carbon atoms; and $R^5$ is a straight or branched chain saturated, partially unsaturated, or unsaturated hydrocarbon of 1 to 6 carbon atoms, or benzyl.

The 2-amino-3,4-dihydropyridines of the present invention are produced by reacting a 2-amino-1,4-dihydropyridine of the formula:

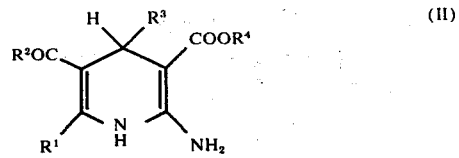

wherein
$R^1$, $R^2$, $R^3$ and $R^4$ are as above defined, with an alkylating agent of the formula:

$$R^5X \qquad (III)$$

wherein
$R^5$ is as above defined, and
X is a moiety capable of being cleaved during the alkylation reaction, in the presence of an inert organic solvent at a temperature of from 20° C to 200° C.

The compounds of the present invention are useful for their antihypertensive and coronary dilating effects. These compounds have been found to exhibit strong and long-lasting antihypertensive effects and strong and long-lasting coronary dilating effects.

It is surprising that the compounds of the present invention are produced in such good yields and in such high purity by the reaction set forth above since according to the prior art, the formation of N-alkylation products of the formula IV or V, below, would have been expected:

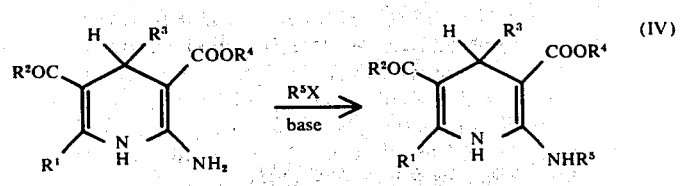

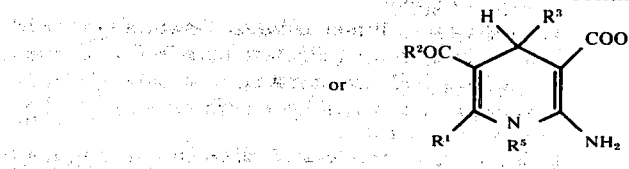

(compare A. E. Tschitschibabin, R. A. Konowalowa and A. A. Konowalowa, Ber. 54, 841 (1921)).

However, the process of the present invention described above yields only the C-alkylation products of formula I, with relocation of the double bond from the 2,3-position of the starting material to the 1,2-position of the final product.

The process of the present invention is particularly advantageous because it makes possible both high yields of the compounds of the present invention and yields of such compounds in a high degree of purity. In addition, the process is carried out as a one-stage process, thus requiring little technical effort. It is also highly economical.

The course of the process of the present invention, when 2-amino-6-methyl-4-(3'-nitrophenyl)-1,4-dihydropyridine3,5-dicarboxylic acid diethyl ester and methyl iodide are reacted in the presence of an alkali metal alcoholate, is illustrated by the following equation;

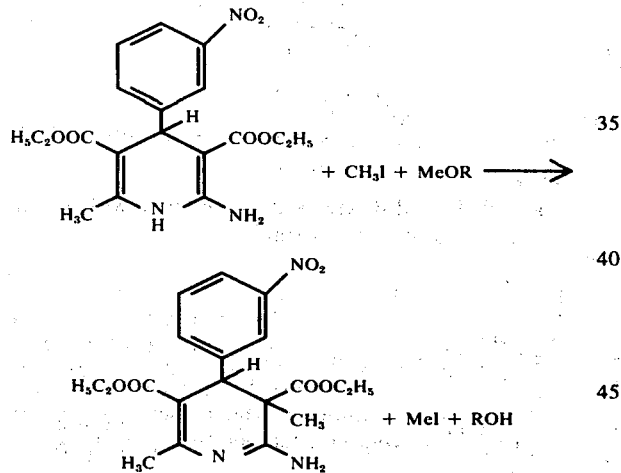

wherein

R is lower alkyl, especially ethyl.

According to one embodiment of the present invention:

R¹ is hydrogen, straight or branched chain lower alkyl, or amino;

R² is straight or branched chain lower alkyl or OR' wherein R' is straight or branched chain lower alkyl, lower alkenyl, lower alkinyl or lower alkyl, lower alkenyl or lower alkinyl interrupted by 1 or 2 carbon atoms;

R³ is straight or branched chain alkyl of 1 to 6 carbon atoms; straight or branched chain alkenyl of 2 to 6 carbon atoms; straight or branched chain alkinyl of 2 to 6 carbon atoms; cycloalkyl of 3 to 6 carbon atoms; cycloalkenyl of 3 to 6 carbon atoms; aryl of 6 to 10 carbon atoms unsubstituted or substituted by 1, 2 or 3 of the same or different substituents selected from the group consisting of alkyl of 1 to 4 carbon atoms, alkoxy of 1 to 4 carbon atoms, halogen, azido, cyano, phenyl, nitro, trifluoromethyl, carbalkoxy of 1 to 4 carbon atoms in the alkoxy moiety and $SO_n$-alkyl of 1 to 4 carbon atoms in the alkyl moiety wherein n is 0, 1 or 2; quinolyl; isoquinolyl; pyridyl; pyrimidyl; thenyl; furyl; or pyrryl;

R⁴ is straight or branched chain alkyl of 1 to 6 carbon atoms, straight or branched chain alkenyl of 2 to 6 carbon atoms, or straight or branched chain alkinyl of 2 to 6 carbon atoms; and R⁵ is straight or branched chain alkyl of 1 to 6 carbon atoms, straight or branched chain alkenyl of 2 to 6 carbon atoms, straight or branched chain alkinyl of 2 to 6 carbon atoms, or benzyl.

According to another embodiment of the present invention:

R¹ is straight or branched chain alkyl of 1 to 4 carbon atoms, or amino;

R² is straight or branched chain alkyl of 1 to 4 carbon atoms, or OR' wherein R' is straight or branched chain alkyl of 1 to 4 carbon atoms, straight or branched chain alkenyl of 2 to 4 carbon atoms, straight or branched chain alkinyl of 2 to 4 carbon atoms, straight or branched chain alkyl of 1 to 4 carbon atoms interrupted by one oxygen atom or straight or branched chain alkenyl of 2 to 4 carbon atoms interrupted by one oxygen atom;

R³ is straight or branched chain alkyl of 1 to 6 carbon atoms; straight or branched chain alkenyl of 2 to 6 carbon atoms; straight or branched chain alkinyl of 2 to 6 carbon atoms; cycloalkyl of 3 to 6 carbon atoms; phenyl unsubstituted or substituted by 1 or 2 of the same or different substituents selected from the group consisting of alkyl of 1 to 4 carbon atoms, alkoxy of 1 to 4 carbon atoms, halogen, azido, cyano, nitro, trifluoromethyl, carbalkoxy of 1 to 4 carbon atoms in the alkoxy moiety and $SO_n$-alkyl of 1 to 4 carbon atoms in the alkyl moiety wherein n is 0, 1 or 2; naphthyl; quinolyl; isoquinolyl; pyridyl; pyrimidyl; thenyl; or furyl;

R⁴ is straight or branched chain alkyl of 1 to 4 carbon atoms, straight or branched chain alkenyl of 2 to 4 carbon atoms or straight or branched chain alkinyl of 2 to 4 carbon atoms; and R⁵ is straight or branched chain alkyl of 1 to 4 carbon atoms, straight or branched chain alkenyl of 2 to 4 carbon atoms, straight or branched chain alkinyl of 2 to 4 carbon atoms, or benzyl.

According to another embodiment of the present invention:

R¹ is straight or branched chin alkyl of 1 to 4 carbon atoms, or amino;

R² is straight or branched chain alkyl of 1 to 4 carbon atoms, or OR' wherein R' is straight or branched chain alkyl of 1 to 4 carbon atoms, straight or branched chain alkenyl of 2 to 4 carbon atoms, straight or branched chain alkyl of 1 to 4 carbon atoms interrupted by one oxygen atom, or straight or branched chain alkenyl of 2 to 4 carbon atoms interrupted by one oxygen atom;

$R^3$ is straight or branched chain alkyl of 1 to 6 carbon atoms, or phenyl unsubstituted or substituted by alkyl of 1 or 2 carbon atoms, alkoxy of 1 or 2 carbon atoms, fluorine, chlorine, bromine, cyano, nitro, trifluoromethyl, or thioalkyl of 1 to 4 carbon atoms;

$R^4$ is straight or branched chain alkyl of 1 to 4 carbon atoms; and $R^5$ is straight or branched chain alkyl of 1 to 4 carbon atoms, or benzyl.

According to another embodiment of the present invention:

$R^1$ is alkyl of 1 or 2 carbon atoms, or amino;

$R^2$ is alkoxy of 1 to 4 carbon atoms;

$R^3$ is alkyl of 1 or 2 carbon atoms, or phenyl unsubstituted or substituted by alkyl of 1 or 2 carbon atoms, chlorine, bromine, cyano, nitro, or thioalkyl of 1 or 2 carbon atoms;

$R^4$ is straight or branched chain alkyl of 1 to 4 carbon atoms; and $R^5$ is straight or branched chain alkyl of 1 to 4 carbon atoms, or benzyl.

According to another embodiment of the present invention:

$R^1$ is methyl, or amino;

$R^2$ is ethoxy, or propoxy;

$R^3$ is methyl, phenyl, nitrophenyl, thiomethylphenyl, or cyanophenyl;

$R^4$ is ethyl, or isopropyl; and $R^5$ is methyl, ethyl, or benzyl.

The 2-amino-1,4-dihydropyridines of the formula II used as starting substances in the process of the present invention are not per se known but can be prepared by one of the following methods:

a. Reaction of an α,β-unsaturated dicarbonyl compound with an amidinoacetic acid ester:

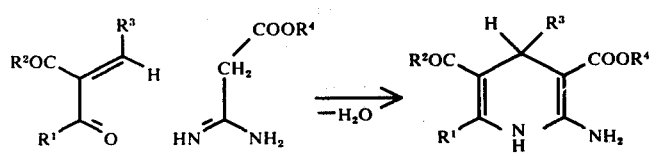

b. Reaction of an aldehyde with a twice-molar amount of an amidinoacetic acid ester:

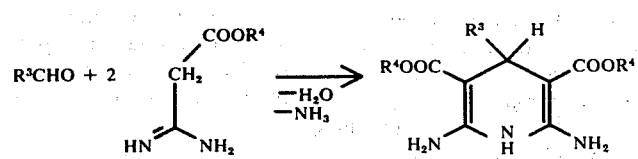

II ($R^1 = NH_2$, $R^2 = OR^4$)

c. Reaction of an α-β-unsaturated β-ketonitrile with an amidinoacetic acid ester:

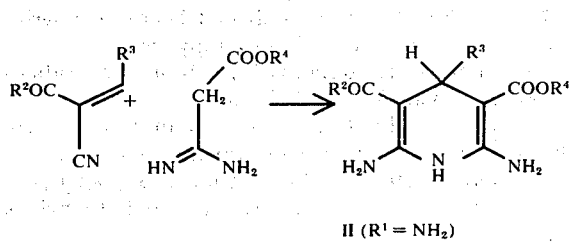

II ($R^1 = NH_2$)

The amidinoacetic acid esters (S. M. McElvain and B. E. Tate, J.A.C.S. 73, 2760 (1951)) and the α,β-unsaturated compounds (org. Reactions XV, 204 et seq.) can be prepared by known methods.

Representative 2-amino- (or 2,6-diamino)-1,4-dihydropyridines (II) include:

2-amino-6-methyl-4-phenyl-1,4-dihydropyridine-3,5-dicarboxylic acid diethyl ester, 2,6-diamino-4-phenyl-1,4-dihydropyridine-3,5-dicarboxylic acid diethyl ester, 2,6-diamino-4-(α-pyridyl)-3,5-dicarboxylic acid diisopropyl ester, 2-amino-6-ethyl-4-(2'-cyanophenyl)-1,4-dihydropyridine3,5-dicarboxylic acid diethyl ester, 2-amino-6-methyl-5-acetyl-4-(3'-nitrophenyl)-3-carboxylic acid ethyl ester, 2-amino-6-methyl-4-(3'-nitrophenyl)-3,5-dicarboxylic acid 3-ethyl ester-5-propargyl ester, 2-amino-6-methyl-4-(3'-trifluoromethylphenyl)-1,4-dihydropyridine-3-ethylester-5-β-methoxyethyl ester, 2-amino-6-methyl-4-(biphenyl-2')-1,4-dihydropyridine-3,5-dicarboxylic acid diethyl ester, 2-amino-6-methyl-4-(2'-methoxyphenyl)-1,4-dihydropyridine-3,5-dicarboxylic acid 3-isopropyl ester-5-ethyl ester, 2-amino-6-ethyl-4-(2'-fluorophenyl)-1,4-dihydropyridine-3,5-dicarboxylic acid 3-ethyl ester-5-isopropyl ester, 2,6-diamino-4-(3'-azidophenyl)-1,4-dihydropyridine-3,5-dicarboxylic acid diethyl ester, 2-amino-6-isopropyl-4-(naphthyl-1')-1,4-dihydropyridine-3,5-dicarboxylic acid 3-isopropyl ester-5-allyl ester, 2,6-diamino-4-(4'-mercaptomethylphenyl)-1,4-dihydropyridine-3,5-dicarboxylic acid diisopropyl ester, 2,6-diamino-4-phenyl-1,4-dihydropyridine-3,5-dicarboxylic acid 3-ethyl ester-5-isopropyl ester, 2-amino-6-methyl-4-(3'-carboxymethylphenyl)-1,4-dihydropyridine-3,5-dicarboxylic acid diethyl ester, 2-amino-6-methyl-4-(quinolyl-4')-1,4-dihydropyridine-3,5-dicarboxylic acid diisopropyl ester, 2,6-diamino-4-(isoquinolyl-1')-1,4-dihydropyridine-3,5-dicarboxylic acid diethyl ester, 2-amino-6-methyl-4-(3'-nitro-6'-chlorophenyl)-1,4-dihydropyridine-3-ethyl ester-5-methyl ester, 2-amino-6-methyl-4-(3',4',5'-trimethoxyphenyl)-1,4-dihydropyridine-3,5-dicarboxylic acid diethyl ester, 2,6-diamino-4-(pyrimidyl-2')-1,4-dihydropyridine-3,5-dicarboxylic acid diethyl ester, 2-amino-6-methyl-4-(furyl-2')-1,4-dihydropyridine-3,5-dicarboxylic acid 3-methyl ester-5-ethyl ester, 2-amino-6-methyl-4-(thenyl-2')-1,4-dihydropyridine-3,5-dicarboxylic acid 3-ethyl ester-5-isopropyl ester, and 2-amino-4-(3'-nitrophenyl)-1,4-dihydropyridine-3,5-dicarboxylic acid 3-allyl ester.

X is preferably chlorine, bromine, iodine, a sulphuric acid ester of the formula -O-SO$_2$OR$^5$ wherein R$^5$ is as above defined, a sulphonic acid of the formula -OSO$_2$R$^6$ wherein R$^6$ is aryl of 6 to 10 carbon atoms especially mono-aryl, or lower alkyl, a phosphonic acid ester of the formula -OPO(OR$^5$)$_2$ wherein R$^5$ is as above defined or dialkyloxonium of the formula

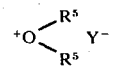

wherein Y$^\ominus$ is BF$_4$$^\ominus$, and R$^5$ is alkyl of 1 to 6 carbon atoms.

The alkylating agents of the formula III are either known per se or can be prepared according to techniques per se known.

Representative alkylating agents (III) which are used in the process of the present invention include:
methyl chloride, bromide and iodide,
ethyl chloride, bromide and iodide,
isopropyl bromide,
n-propyl iodide,
n-butyl bromide,
2-iodopentane
benzyl chloride, bromide and iodide,
methyl, ethyl and n-propyl tosylates,
dimethyl, diethyl, dipropyl and dibutyl sulphates,
triethyl phosphate, and
triethyloxonium fluoborate.

The process of the present invention is preferably carried out in the presence of a basic reagent. Preferred basic reagents include alkali metal alcoholates in stoichiometric proportions, amines, alkali metal corbonates and alkaline earth metal carbonates.

Any inert organic solvent can be used as a suitable diluent. Preferred solvents include alcohols such as methanol, ethanol and propanol, ethers such as dioxane and diethyl ether, pyridine, dimethylformamide, dimethylsulphoxide and acetonitrile.

The reaction temperatures can be varied within a substantial range as indicated above. The preferred temperature range is between 50° C and 150° C and especially at the boiling point of the solvent.

The process of the present invention may be carried out under atmospheric pressure or under elevated pressure. It is preferred that atmospheric pressure be used.

In carrying out the process of the present invention, the reactants are usually employed in molar amounts but a slight excess of alkylating agent is not objectionable.

The compounds of the present invention have demonstrated the following activity in test animals:

1. On parenteral, oral and perlingual administration the new compounds produce a distinct and long-lasting dilation of the coronary vessels. This action on the coronary vessels is intensified by a simultaneous nitrite-like effect of reducing the load on the heart. They influence or modify the heart metabolism in the sense of an energy saving.

2. The new compounds lower the blood pressure of normotonic and hypertonic animals and can thus be used as antihypertensive agents.

3. The excitability of the stimulus formation and excitation conduction system within the heart is lowered, so that an anti-fibrillation action demonstrable at therapeutic doses results.

4. The tone of the smooth muscle of the vessels is greatly reduced under the action of the compounds. This vascular-spasmolytic action can take place throughout the entire vascular system or can manifest itself more or less isolated in circumscribed vascular regions (for example, the central nervous system).

5. The new compounds have strong muscular-spasmolytic actions which manifest themselves on the smooth muscle of the stomach, the intestinal tract, the urogenital tract and the respiratory system.

6. The new compounds influence the cholesterol level and lipid level of the blood.

The coronary action of the compounds of the present invention prepared in the following examples is shown by way of illustration in Table I:

Table I

| Compound of Example No. | Distinctly discernible rise in oxygen saturation in the coronary sinus | |
|---|---|---|
| | Dose | Duration of action |
| 1 | 2.0 mg/kg body wt. | 20 minutes |
| 1a | 0.1 mg/kg body wt. | 45 minutes |
| 1b | 2.0 mg/kg body wt. | 3 minutes |
| 1d | 0.5 mg/kg body wt. | 60 minutes |
| 1f | 0.5 mg/kg body wt. | >120 minutes |
| 2 | 5.0 mg/kg. body wt. | 45 minutes |
| 3 | 3.0 mg/kg body wt. | 20 minutes |
| 4 | 2.0 mg/kg body wt. | 20 minutes |

The coronary action was determined on narcotised, heart-catheterised mongrel dogs by measuring the rise in oxygen saturation in the coronary sinus after intravenous administration of the compounds.

The action of some compounds according to the invention on the blood pressure can be seen from Table II. The dose quoted in the second column relates to a blood pressure lowering of at least 15 mm Hg.

Table II

| Compound of Example No. | Toxicity in mice: mg/kg administered orally | Blood pressure lowering in hypertonic rats: mg/kg administered orally |
|---|---|---|
| 1 | >3,000 | from 31.5 |
| 1f | — | from 1.0 |
| 4 | 3,000 | from 31.5 |

The pharmaceutical compositions of the present invention contain a major or minor amount e.g. 0.1 to 99.5%, preferably 0.5 to 90% of at least one 2-amino-3,4-dihydropyridine as above defined in combination with a pharmaceutically acceptable nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage administered intravenously will be from 0.01 to 10 mg/kg, preferably 0.1 to 5 mg/kg, of body weight per day, and the dosage administered orally will be from 0.1 to 50 mg/kg, preferably 1 to 20 mg/kg, of body weight per day. In some instances a sufficient therapeutic effect can be obtained at a lower dose while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and-/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semi-liquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose for intravenous administration is 0.5 mg to 1.0 g, especially 5 mg to 500 mg, of active ingredient; the preferred daily dose for oral administration is 5 mg to 5.0 g, especially 50 mg to 2.0 g, of active ingredient. The preferred administration is oral or intravenous.

The following non-limitative examples more particularly illustrate the present invention:

EXAMPLE 1

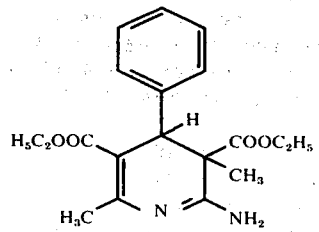

A solution of 33.0 g of 2-amino-6-methyl-4-phenyl-1,4-dihydropyridine-3,5-dicarboxylic acid diethyl ester and 6.8 g of sodium ethylate in 500 ml of ethanol is brought to the boil and treated with 15 g of methyl iodide. After boiling for a further 60 minutes under reflux, the mixture is concentrated by distillation and the residue is taken up in 300 ml of chloroform and extracted by shaking twice with 100 ml of water. Concentration of the organic phase and recrystallization from ethanol gives 18.6 g (54% of theory) of 2-amino-3,6-dimethyl-4-phenyl-3,4-dihydropyridine-3,5-dicarboxylic acid diethyl ester of melting point 139° C.

EXAMPLE 1a

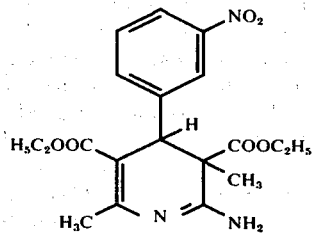

In a manner analogous to that set forth in Example 1 above, 37.4 g of 2-amino-6-methyl-4-(3'-nitrophenyl)-1,4-dihydropyridine-3,5-dicarboxylic acid diethyl ester, 6.8 g of sodium ethylate and 15 g of methyl iodide in 500 ml of ethanol gave 2-amino-3,6-dimethyl-4-(3'-nitrophenyl)-3,4-dihydropyridine-3,5-dicarboxylic acid diethyl ester of melting point 115° C (19.8 g, 51% of theory).

EXAMPLE 1b

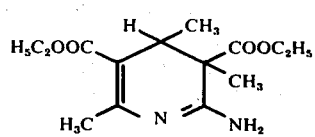

In a manner analogous to that set forth in Example 1 above, 26.7 g of 2-amino-4,6-dimethyl-1,4-dihydropyridine-3,5-dicarboxylic acid diethyl ester, 6.8 g of sodium ethylate and 15 g of methyl iodide in 300 ml of ethanol gave 2-amino-3,4,6-trimethyl-3,4-dihydropyridine-3,5-dicarboxylic acid diethyl ester of melting point 121° C (17.7 g, 62% of theory).

EXAMPLE 1c

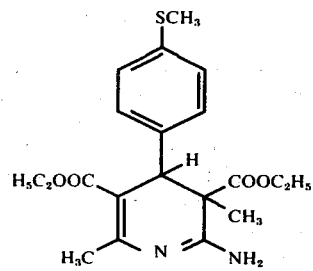

In a manner analogous to that set forth in Example 1 above, 37.5 g of 2-amino-6-methyl-4-(4'-methylmercaptophenyl)-1,4-dihydropyridine-3,5-dicarboxylic acid diethyl ester, 6.8 g of sodium ethylate and 15 g of methyl iodide in 600 ml of ethanol gave 2-amino-3,6-dimethyl-4-(4'-methylmercaptophenyl)-3,4-dihydropyridine-3,5-dicarboxylic acid diethyl ester of melting point 158° C (22.2 g, 57% of theory).

EXAMPLE 1d

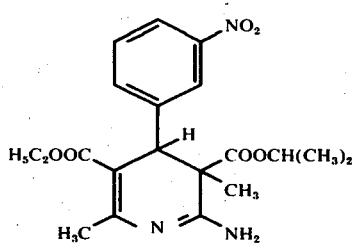

In a manner analogous to that set forth in Example 1 above, 11.7 g of 2-amino-6-methyl-4-(3'-nitrophenyl)-1,4-dihydropyridine-3,5-dicarboxylic acid 3-isopropyl ester-5-ethyl ester, 2.1 g of sodium ethylate and 5 g of methyl iodide in 150 ml of ethanol gave 2-amino-3,6-dimethyl-4-(3'-nitrophenyl)-3,4-dihydropyridine-3,5-dicarboxylic acid 3-isopropyl ester-5-ethyl ester of melting point 114° C (4.7 g, 39% of theory).

EXAMPLE 1e

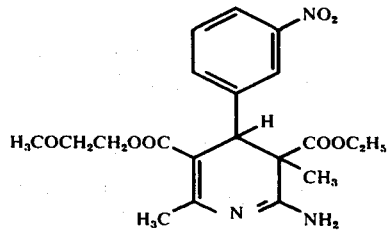

In a manner analogous to that set forth in Example 1 above, 6.8 g of 2-amino-6-methyl-4-(3'-nitrophenyl)-1,4-dihydropyridine-3,5-dicarboxylic acid 3-ethyl ester-5-β-methoxyethyl ester, 1.2 g of sodium ethylate and 2.5 g of methyl iodide in 80 ml of ethanol gave 2-amino-3,6-dimethyl-4-(3'-nitrophenyl)-3,4-dihydropyridine-3,5-dicarboxylic acid 3-ethyl ester-5-β-methoxyethyl ester of melting point 117° C (4.1 g, 56% of theory).

EXAMPLE 1f

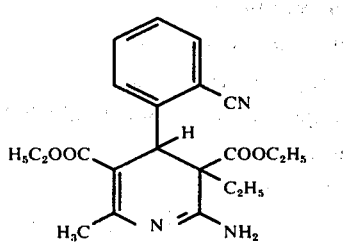

In a manner analogous to that set forth in Example 1 above, 36.5 g of 2-amino-6-methyl-4-(2'-cyanophenyl)-1,4-dihydropyridine-3,5-dicarboxylic acid diethyl ester, 6.8 g of sodium ethylate and 15 g of methyl iodide in 600 ml of ethanol gave 2-amino-3,6-dimethyl-4-(2'-cyanophenyl)-3,4-dihydropyridine-3,5-dicarboxylic acid diethyl ester of melting point 169° C (26 g, 68% of theory).

EXAMPLE 2

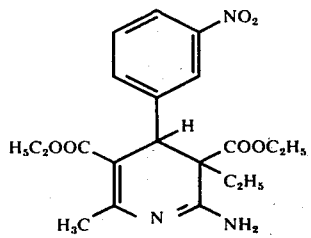

A solution of 37.4 g of 2-amino-6-methyl-4-(3'-nitrophenyl)-1,4-dihydropyridine-3,5-dicarboxylic acid diethyl ester and 6.8 g of sodium ethylate in 500 ml of ethanol is brought to the boil and treated with 10.9 g of ethyl bromide. After boiling for a further 60 minutes under reflux, the mixture is concentrated by distillation and the residue is taken up in 300 ml of chloroform and extracted by shaking twice with 100 ml of water. Concentration of the organic phase and recrystallization from ethanol gave 2-amino-3-ethyl-6-methyl-4-(3'-nitrophenyl)-3,4-dihydropyridine-3,5-dicarboxylic acid diethyl ester of melting point 122°-3° C (16.5 g, 41% of theory).

EXAMPLE 3

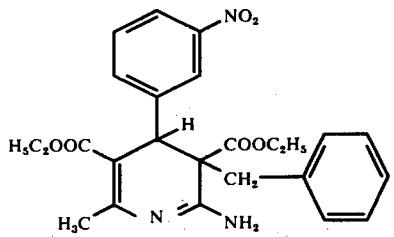

A solution of 37.4 g of 2-amino-6-methyl-4-(3'-nitrophenyl)-1,4-dihydropyridine-3,5-dicarboxylic acid diethyl ester and 6.8 g of sodium ethylate in 500 ml of ethanol is brought to the boil and treated with 17.1 g of benzyl bromide. After boiling for a further 60 minutes under reflux, the mixture is concentrated by distillation and the residue is taken up in 300 ml of chloroform and extracted by shaking twice with 100 ml of water. Concentration of the organic phase and recrystallization from ethanol gave 2-amino-3-benzyl-6-methyl-4-(3'-nitrophenyl)-3,4-dihydropyridine-3,5-dicarboxylic acid diethyl ester of melting point 208° C (29.4 g, 63% of theory).

EXAMPLE 4

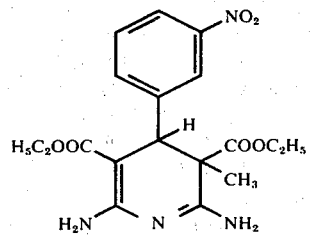

A solution of 37.5 g of 2,6-diamino-4-(3'-nitrophenyl)-1,4-dihydropyridine-3,5-dicarboxylic acid diethyl ester and 6.8 g of sodium ethylate in 500 ml of ethanol was treated with 15 g of methyl iodide at the boil. After a further 60 minutes under reflux, the mixture was concentrated by distillation. The residue is taken up in 300 ml of chloroform and extracted by shaking twice with 100 ml of water, and the organic phase is concentrated. Recrystallization of the residue from ethanol gave 2.6-diamino-3-methyl-4-(3'-nitrophenyl)-3,4-dihydropyridine-3,5-dicarboxylic acid diethyl ester of melting point 142° C (18 g, 41.5% of theory).

What is claimed is:

1. A pharmaceutical composition useful for effecting coronary vessel dilation in humans and other animals and for treating hypertension in humans and other animals which comprises a coronary vessel dilating amount or an antihypertensive amount of a compound of the formula:

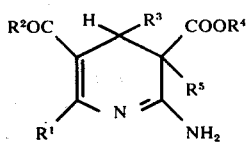

wherein
$R^1$ is hydrogen, straight or branched chain lower alkyl, or amino;
$R^2$ is straight or branched chain lower alkyl or OR' wherein R' is straight or branched chain lower alkyl, lower alkenyl, lower alkynyl or alkoxyalkyl of 2 to 4 carbon atoms;
$R^3$ is straight or branched chain alkyl of 1 to 6 carbon atoms; straight or branched chain alkenyl of 2 to 6 carbon atoms; straight or branched chain alkynyl of 2 to 6 carbon atoms; or unsubstituted or substituted phenyl or naphthyl which when substituted bears 1, 2 or 3 of the same or different substituents selected from the group consisting of alkyl of 1 to 4 carbon atoms, alkoxy of 1 to 4 carbon atoms, halogen, azido, cyano, phenyl, nitro, trifluoromethyl, carbalkoxy of 1 to 4 carbon atoms in the alkoxy moiety and $SO_n$-alkyl of 1 to 4 carbon atoms in the alkyl moiety wherein n is 0, 1 or 2;
$R^4$ is straight or branched chain alkyl of 1 to 6 carbon atoms, straight or branched chain alkenyl of 2 to 6 carbon atoms, or straight or branched chain alkynyl of 2 to 6 carbon atoms; and

R⁵ is straight or branched chain alkyl of 1 to 6 carbon atoms, straight or branched chain alkenyl of 2 to 6 carbon atoms, straight or branched chain alkynyl of 2 to 6 carbon atoms, or benzyl, in combination with a pharmaceutical acceptable non-toxic inert carrier.

2. A composition according to claim 1 wherein
R¹ is straight or branched chain alkyl of 1 to 4 carbon atoms, or amino;
R² is straight or branched chain alkyl of 1 to 4 carbon atoms, or OR' wherein R' is straight or branched chain alkyl of 1 to 4 carbon atoms, straight or branched chain alkenyl of 2 to 4 carbon atoms, straight or branched chain alkynyl of 2 to 4 carbon atoms, or alkoxyalkyl of 2 to 4 carbon atoms;
R³ is straight or branched chain alkyl of 1 to 6 carbon atoms; straight or branched chain alkenyl of 2 to 6 carbon atoms; straight or branched chain alkynyl of 2 to 6 carbon atoms; phenyl unsubstituted or substituted by 1 or 2 of the same or different substituents selected from the group consisting of alkyl of 1 to 4 carbon atoms, alkoxy of 1 to 4 carbon atoms, halogen, azido, cyano, nitro, trifluoromethyl, carbalkoxy of 1 to 4 carbon atoms in the alkoxy moiety and SO$_n$-alkyl of 1 to 4 carbon atoms in the alkyl moiety wherein $n$ is 0, 1 or 2; or naphthyl;
R⁴ is straight or branched chain alkyl of 1 to 4 carbon atoms, straight or branched chain alkenyl of 2 to 4 carbon atoms or straight or branched chain alkynyl of 2 to 4 carbon atoms; and
R⁵ is straight or branched chain alkyl of 1 to 4 carbon atoms, straight or branched chain alkenyl of 2 to 4 carbon atoms, straight or branched chain alkynyl of 2 to 4 carbon atoms, or benzyl.

3. A composition according to claim 1 wherein
R¹ is straight or branched chain alkyl of 1 to 4 carbon atoms, or amino;
R² is straight or branched chain alkyl of 1 to 4 carbon atoms, or OR' wherein R' is straight or branched chain alkyl of 1 to 4 carbon atoms, straight or branched chain alkenyl of 2 to 4 carbon atoms, or alkoxyalkyl of 2 to 4 carbon atoms;
R³ is straight or branched chain alkyl of 1 to 6 carbon atoms, or phenyl unsubstituted or substituted by alkyl of 1 or 2 carbon atoms, alkoxy of 1 or 2 carbon atoms, fluorine, chlorine, bromine, cyano, nitro, trifluoromethyl, or thioalkyl of 1 to 4 carbon atoms;
R⁴ is straight or branched chain alkyl of 1 to 4 carbon atoms; and
R⁵ is straight or branched chain alkyl of 1 to 4 carbon atoms, or benzyl.

4. A composition according to claim 1 wherein
R¹ is alkyl of 1 or 2 carbon atoms, or amino;
R² is alkoxy of 1 to 4 carbon atoms;
R³ is alkyl of 1 or 2 carbon atoms, or phenyl unsubstituted or substituted by alkyl of 1 or 2 carbon atoms, chlorine, bromine, cyano, nitro, or thioalkyl of 1 or 2 carbon atoms;
R⁴ is straight or branched chain alkyl of 1 to 4 carbon atoms; and
R⁵ is straight or branched chain alkyl of 1 to 4 carbon atoms, or benzyl.

5. A composition according to claim 1 wherein
R¹ is methyl, or amino;

R² is ethoxy, or propoxy;
R³ is methyl, phenyl, nitrophenyl, thiomethylphenyl, or cyanophenyl;
R⁴ is ethyl, or isopropyl; and
R⁵ is methyl, ethyl, or benzyl.

6. A composition according to claim 1 wherein the compound is

[chemical structure]

7. A composition according to claim 1 wherein the compound is

[chemical structure]

8. A composition according to claim 1 wherein the compound is

[chemical structure]

9. A composition according to claim 1 wherein the compound is

[chemical structure]

10. A composition according to claim 1 wherein the compound is

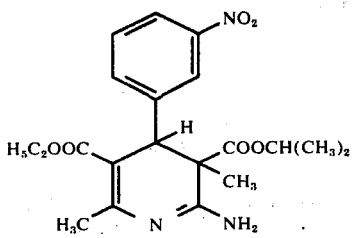

11. A composition according to claim 1 wherein the compound is

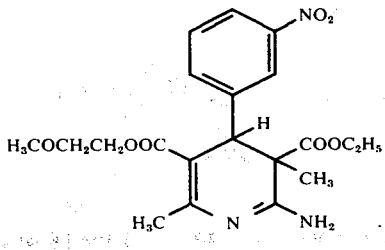

12. A composition according to claim 1 wherein the compound is

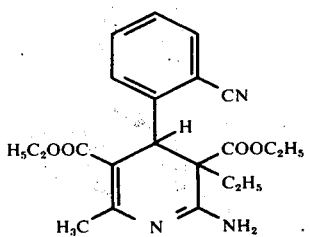

13. A composition according to claim 1 wherein the compound is

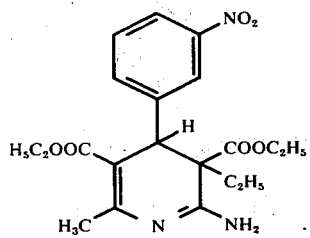

14. A composition according to claim 1 wherein the compound is

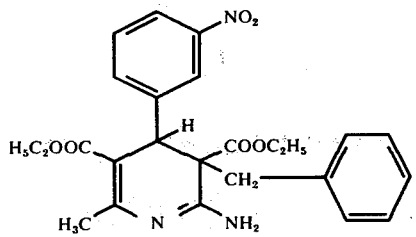

15. A composition according to claim 1 wherein the compound is

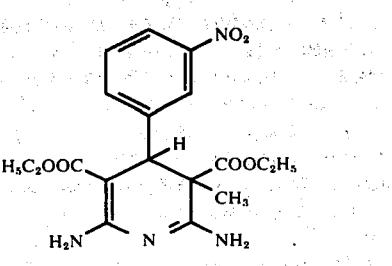

16. A composition according to claim 1 in oral administration form.

17. A composition according to claim 1 in parenteral administration form.

18. A method of effecting coronary vessel dilation in humans and other animals and treating hypertension in humans and other animals which comprises administering to such human or animal a coronary vessel dilating amount or an antihypertensive amount of a compound of the formula:

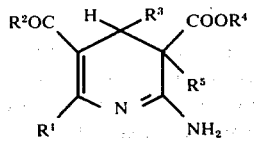

wherein $R^1$ is hydrogen, straight or branched chain lower alkyl, or amino;

$R^2$ is straight or branched chain lower alkyl or OR' wherein R' is straight or branched chain lower alkyl, lower alkenyl, lower alkynyl or alkoxyalkyl of 2 to 4 carbon atoms;

$R^3$ is straight or branched chain alkyl of 1 to 6 carbon atoms; straight or branched chain alkenyl of 2 to 6 carbon atoms; straight or branched chain alkynyl of 2 to 6 carbon atoms; or unsubstituted or substituted phenyl or naphthyl which when substituted bears 1, 2 or 3 of the same or different substituents selected from the group consisting of alkyl of 1 to 4 carbon atoms, alkoxy of 1 to 4 carbon atoms, halogen, azido, cyano, phenyl, nitro, trifluoromethyl, carbalkoxy of 1 to 4 carbon atoms in the alkoxy moiety and $SO_n$-alkyl of 1 to 4 carbon atoms in the alkyl moiety wherein n is 0, 1 or 2;

$R^4$ is straight or branched chain alkyl of 1 to 6 carbon atoms, straight or branched chain alkenyl of 2 to 6 carbon atoms, or straight or branched chain alkynyl of 2 to 6 carbon atoms; and $R^5$ is straight or branched chain alkyl of 1 to 6 carbon atoms, straight or branched chain alkenyl of 2 to 6 carbon atoms, straight or branched chain alkynyl of 2 to 6 carbon atoms, or benzyl.

19. A method according to claim 18 wherein $R^1$ is straight or branched chain alkyl of 1 to 4 carbon atoms, or amino;

$R^2$ is straight or branched chain alkyl of 1 to 4 carbon atoms, or OR' wherein R' is straight or branched chain alkyl of 1 to 4 carbon atoms, straight or branched chain alkenyl of 2 to 4 carbon atoms, straight or branched chain alkynyl of 2 to 4 carbon atoms, or alkoxyalkyl of 2 to 4 carbon atoms;

$R^3$ is straight or branched chain alkyl of 1 to 6 carbon atoms; straight or branched chain alkenyl of 2 to 6 carbon atoms; straight or branched chain alkynyl of 2 to 6 carbon atoms; phenyl unsubstituted or substituted by 1 or 2 of the same or different substituents selected from the group consisting of alkyl of 1 to 4 carbon atoms, alkoxy of 1 to 4 carbon atoms, halogen, azido, cyano, nitro, trifluoromethyl, carbalkoxy of 1 to 4 carbon atoms in the alkoxy moiety and $SO_n$-alkyl of 1 to 4 carbon atoms in the alkyl moiety wherein $n$ is 0, 1 or 2; or naphthyl;

$R^4$ is straight or branched chain alkyl of 1 to 4 carbon atoms, straight or branched chain alkenyl of 2 to 4 carbon atoms or straight or branched chain alkynyl of 2 to 4 carbon atoms; and $R^5$ is straight or branched chain alkyl of 1 to 4 carbon atoms, straight or branched chain alkenyl of 2 to 4 carbon atoms, straight or branched chain alkynyl of 2 to 4 carbon atoms, or benzyl.

20. A method according to claim 18 wherein $R^1$ is straight or branched chain alkyl of 1 to 4 carbon atoms, or amino;

$R^2$ is straight or branched chain alkyl of 1 to 4 carbon atoms, or $OR'$ wherein $R'$ is straight or branched chain alkyl of 1 to 4 carbon atoms, straight or branched chain alkenyl of 2 to 4 carbon atoms, or alkoxyalkyl of 2 to 4 carbon atoms;

$R^3$ is straight or branched chain alkyl of 1 to 6 carbon atoms, or phenyl unsubstituted or substituted by alkyl of 1 or 2 carbon atoms, alkoxy of 1 or 2 carbon atoms, fluorine, chlorine, bromine, cyano, nitro, trifluoromethyl, or thioalkyl of 1 to 4 carbon atoms;

$R^4$ is straight or branched chain alkyl of 1 to 4 carbon atoms; and $R^5$ is straight or branched chain alkyl of 1 to 4 carbon atoms, or benzyl.

21. A method according to claim 18 wherein $R^1$ is alkyl of 1 or 2 carbon atoms, or amino;

$R^2$ is alkoxy of 1 to 4 carbon atoms;

$R^3$ is alkyl of 1 or 2 carbon atoms, or phenyl unsubstituted or substituted by alkyl of 1 or 2 carbon atoms, chlorine, bromine, cyano, nitro, or thioalkyl of 1 or 2 carbon atoms;

$R^4$ is straight or branched chain alkyl of 1 to 4 carbon atoms; and $R^5$ is straight or branched chain alkyl of 1 to 4 carbon atoms, or benzyl.

22. A method according to claim 18 wherein $R^1$ is methyl, or amino;

$R^2$ is ethoxy, or propoxy;

$R^3$ is methyl, phenyl, nitrophenyl, thiomethylphenyl, or cyanophenyl;

$R^4$ is ethyl, or isopropyl; and $R^5$ is methyl, ethyl, or benzyl.

23. A method according to claim 18 wherein the compound is

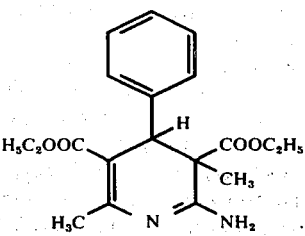

24. A method according to claim 18 wherein the compound is

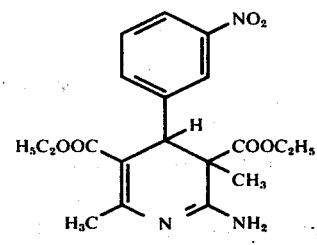

25. A method according to claim 18 wherein the compound is

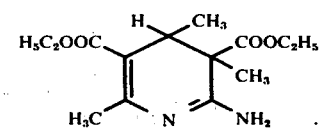

26. A method according to claim 18 wherein the compound is

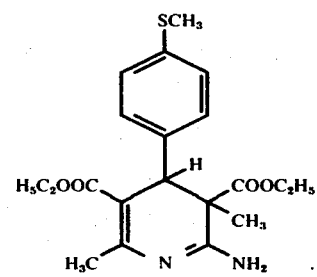

27. A method according to claim 18 wherein the compound is

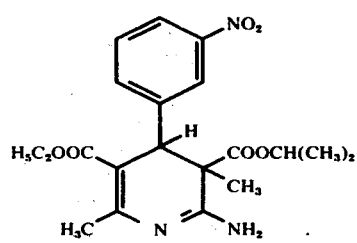

28. A method according to claim 18 wherein the compound is

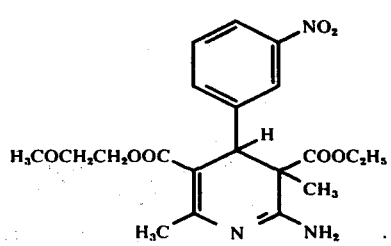

29. A method according to claim 18 wherein the compound is

30. A method according to claim 18 wherein the compound is
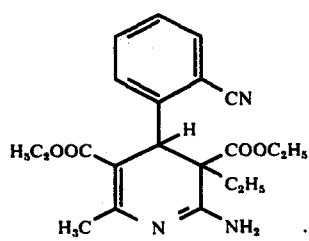
31. A method according to claim 18 wherein the compound is
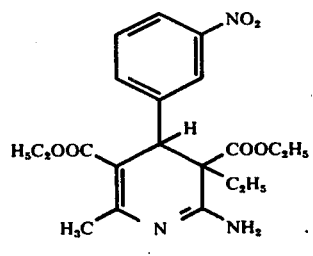
32. A method according to claim 18 wherein the compound is
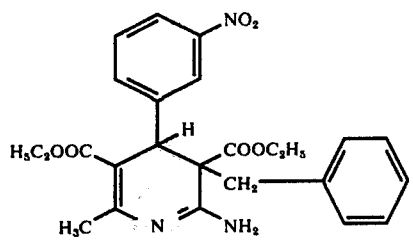
33. A method according to claim 18 wherein the administration is oral.
34. A method according to claim 18 wherein the administration is parenteral.
* * * * *